United States Patent

Elliott et al.

[11] Patent Number: 6,004,915
[45] Date of Patent: *Dec. 21, 1999

[54] CLEANSING COMPOSITIONS

[75] Inventors: Russell Phillip Elliott, Egham; Nicola Jacqueline Phipps, Green Lane, both of United Kingdom

[73] Assignee: The Procter & Gamble Company, Cincinnati, Ohio

[*] Notice: This patent is subject to a terminal disclaimer.

[21] Appl. No.: 08/973,054

[22] PCT Filed: May 9, 1996

[86] PCT No.: PCT/US96/06576

§ 371 Date: Nov. 26, 1997

§ 102(e) Date: Nov. 26, 1997

[87] PCT Pub. No.: WO96/37592

PCT Pub. Date: Nov. 28, 1996

[30] Foreign Application Priority Data

May 27, 1995 [GB] United Kingdom .................. 9510833

[51] Int. Cl.$^6$ .................. C11D 1/83; C11D 3/18
[52] U.S. Cl. .................. 510/135; 510/119; 510/130; 510/417; 510/422; 510/426; 510/427
[58] Field of Search .................. 510/119, 135–138, 510/158, 159, 417, 421–424, 470, 476, 130

[56] References Cited

U.S. PATENT DOCUMENTS

| | | | |
|---|---|---|---|
| 4,368,213 | 1/1983 | Hollenbach et al. | 426/590 |
| 4,435,317 | 3/1984 | Gerritsen et al. | 252/547 |
| 4,446,165 | 5/1984 | Roberts | 426/602 |
| 4,731,201 | 3/1988 | Robbins et al. | 252/551 |
| 4,740,367 | 4/1988 | Force et al. | 424/47 |
| 4,857,213 | 8/1989 | Caswell et al. | 252/8.75 |
| 4,997,641 | 3/1991 | Hartnett et al. | 424/70 |
| 5,078,990 | 1/1992 | Martin et al. | 424/70 |
| 5,106,613 | 4/1992 | Hartnett et al. | 424/71 |
| 5,120,532 | 6/1992 | Wells et al. | 424/70 |
| 5,152,914 | 10/1992 | Forster et al. | 252/174 |
| 5,160,738 | 11/1992 | Macaulay et al. | 424/401 |
| 5,213,716 | 5/1993 | Patel et al. | 252/547 |
| 5,302,322 | 4/1994 | Birtwistle | 252/547 |
| 5,318,728 | 6/1994 | Surutzidis et al. | 252/548 |
| 5,332,528 | 7/1994 | Pan et al. | 252/548 |
| 5,348,736 | 9/1994 | Patel et al. | 424/70 |
| 5,358,667 | 10/1994 | Bergmann | 252/547 |
| 5,395,542 | 3/1995 | Nozaki et al. | 252/174.16 |
| 5,409,640 | 4/1995 | Giret et al. | 252/546 |
| 5,417,893 | 5/1995 | Ofosu-Asante | 252/558 |
| 5,439,615 | 8/1995 | Lefebvre et al. | 252/548 |
| 5,439,682 | 8/1995 | Wivell et al. | 724/401 |
| 5,585,104 | 12/1996 | Ha et al. | 424/401 |

*Primary Examiner*—Yogendra Gupta
*Assistant Examiner*—Gregory E. Webb
*Attorney, Agent, or Firm*—Darryl C. Little

[57] ABSTRACT

A personal cleansing composition comprising: (a) from about 1% to about 25% by weight of water-soluble gel-forming nonionic surfactant; (b) from about 0.1% to about 3% by weight of alkyl sulfate fluidizing agent having an average of from 4 to 10 carbon atoms in the alkyl chain; and (c) optionally, from about 1% to about 30% by weight of a dispersed oil phase. The cleansing products demonstrate excellent low temperature fluidity characteristics, excellent mildness, in-use and after-use conditioning benefits, lathering and rinsibility.

27 Claims, No Drawings

CLEANSING COMPOSITIONS

TECHNICAL FIELD

The present invention relates to cleansing compositions. In particular it relates to mild personal cleansing compositions with good skin feel attributes and foaming properties suitable for simultaneously cleansing and conditioning the skin and/or the hair and which may be used, for example, in the form of foam bath preparations, shower products, skin cleansers, hand, face and body cleansers, shampoos, etc.

BACKGROUND OF THE INVENTION

Mild cosmetic compositions must satisfy a number of criteria including cleansing power, foaming properties and mildness/low irritancy/good feel with respect to the skin, hair and the ocular mucosae. Skin is made up of several layers of cells which coat and protect the keratin and collagen fibrous proteins that form the skeleton of its structure. The outermost of these layers, referred to as the stratum corneum, is known to be composed of 250 Å protein bundles surrounded by 80 Å thick layers. Hair similarly has a protective outer coating enclosing the hair fibre which is called the cuticle. Anionic surfactants can penetrate the stratum corneum membrane and the cuticle and, by delipidization destroy membrane integrity. This interference with skin and hair protective membranes can lead to a rough skin feel and eye irritation and may eventually permit the surfactant to interact with the keratin and hair proteins creating irritation and loss of barrier and water retention functions.

Ideal cosmetic cleansers should cleanse the skin or hair gently, without defatting and/or drying the hair and skin and without irritating the ocular mucosae or leaving skin taut after frequent use. Most lathering soaps, shower and bath products, shampoos and bars fail in this respect.

Certain synthetic surfactants are known to be mild. However, a major drawback of most mild synthetic surfactant systems when formulated for shampooing or personal cleansing is poor lather performance compared to the highest shampoo and bar soap standards. Thus, surfactants that are among the mildest, such as sodium laureth-3 sulphosuccinate, are marginal in lather. The use of known high sudsing anionic surfactants with lather boosters, on the other hand, can yield acceptable lather volume and quality but at the expense of clinical skin mildness. These two facts make the surfactant selection, the lather and mildness benefit formulation process a delicate balancing act.

Despite the many years of research that have been expended by the toiletries industry on personal cleansing, the broad mass of consumers remain dissatisfied by the mildness of present day cleansing compositions, finding, for example, that they have to apply a separate cosmetic lotion or cream moisturizer to the skin after using a shower or bath preparation in order to maintain skin suppleness and hydration and to counteract the delipidizing effect of the cleanser.

It is known from the art that inclusion of oils in bathing compositions can provide post-use skin feel benefits. However incorporation of oils at levels sufficient to deliver consumer noticeable benefits has until now proved to be a challenge, particularly with respect to maintaining good lather characteristics in the presence of oil and avoiding unpleasant 'slimy'/'greasy' water feel or appearance during use while still delivering a desirable after-use soft skin feel. A further difficulty associated with combining high levels of oil with conventional detergent systems has been the achievement of a system in which the oil can be released into the water during use which remains stable over time and across a range of temperature conditions.

Applicant has found that certain oil dispersing nonionic surfactants are valuable in bathing compositions for the delivery of enhanced skin mildness and desirable water aesthetics whilst maintaining a good lather profile. However, Applicant has also found that use of certain oil dispersing nonionic surfactants in bathing compositions can lead to dispensing difficulties under stressed temperature conditions. In particular, Applicant has found that bathing compositions containing certain mild oil-dispersing surfactants demonstrate highly viscous gel-like behaviour under low temperature conditions. It has now been found that personal cleansing compositions having improved skin feel attributes both for in use feel and after use feel, an excellent lather profile and having desirable low temperature fluidity characteristics can be formed by the use of certain oil dispersing nonionic surfactants with auxiliary surfactants and dispersible oils and a fluidising agent in particular levels and ratios.

Thus a need exists for personal cleansing products which will not dehydrate the skin or result in loss of skin suppleness, which will provide a level of skin conditioning performance which previously has only been provided by a separate post-cleansing cosmetic moisturizer and which will produce a foam which is stable and of high quality, which are effective hair and skin cleansers, which have good in-use aesthetics, fluidity and rinsibility characteristics, and which at the same time have stable product and viscosity characteristics and remain fully stable under long term and stressed temperature storage conditions.

SUMMARY OF THE INVENTION

The subject of the present invention is a mild, foam-producing cleansing product suitable for personal cleansing of the skin or hair and which may be used as foam bath and shower products, skin cleansers and shampoos etc. According to one aspect of the invention, there is provided a detergent, personal cleansing or cosmetic composition comprising:
  (a) from about 1% to about 25% by weight of water-soluble gel-forming nonionic surfactant;
  (b) from about 0.1% to about 3% by weight of a alkyl sulphate fluidising agent having an average of from 4 to 10 carbon atoms on the alkyl chain; and
  (c) optionally, from about 1% to about 30% by weight of dispersed oil phase.

In a highly preferred embodiment, the invention takes the form of a foam producing cleansing composition with superior skin feel characteristics, improved perceived dryness and assessed tightness and expertly graded dryness, combined with excellent lathering, good stability, cleansing ability and conditioning performance.

All concentrations and ratios herein are by weight of the cleansing composition, unless otherwise specified. Surfactant chain lengths are also on a weight average chain length basis, unless otherwise specified.

The cleansing compositions herein are based on the combination of water-soluble surfactants, an alkyl sulphate fluidising agent and a dispersed oil phase. In preferred compositions the surfactant system comprises a gel-forming, oil dispersing nonionic surfactant and mild auxiliary surfactants having an average carbon chain length of from about 12 to about 22 carbon atoms, which in general terms can be selected from other nonionic, anionic, amphoteric and zwitterionic surfactants and mixtures thereof. The total level of surfactant, inclusive of anionic, nonionic, zwitterionic, amphoteric and other surfactant components is preferably from about 5% to about 25%, more preferably from about 7% to about 20%, and especially from about 8% to about 16% by weight. The compositions preferably comprise a mixture of gel-forming, oil dispersing nonionic surfactant and anionic surfactants optionally with auxiliary nonionic, zwitterionic and/or amphoteric surfactants. The total level of auxiliary surfactant is in the range from about 0.1% to about 15%, preferably from about 1% to about 10%, more preferably from about 2% to about 6% by weight of the composition, while the level of gel-forming oil dispersing nonionic surfactant is from about 1% to about 25%, preferably from about 2% to about 15%, more preferably from about 3% to about 12% by weight and especially from about 4% to about 8% by weight. The weight ratio of anionic surfactant:auxiliary nonionic, zwitterionic and/or amphoteric surfactant is preferably in the range of from about 5:1 to about 1:3. The ratio of auxiliary surfactant to gel-forming, oil dispersing nonionic surfactant is in the range of from about 1:100 to about 2:1, preferably in the range of from 1:10 to about 10:1, more preferably from about 1:5 to about 5:1, and especially from about 1:3 to about 3:1. The preferred compositions within the scope of the invention comprise mixtures of nonionic surfactants, oil, fluidising agent and auxiliary anionic, zwitterionic and/or amphoteric surfactants, wherein the level of dispersed oil phase is from about 3% to about 25%, preferably from about 5% to about 20%, more preferably from about 8% to about 15% by weight of the composition and the weight ratio of gel-forming, oil dispersing nonionic surfactant : dispersed oil phase is in the range of from 1:20 to about 3:2, preferably from about 1:8 to about 1:1, more preferably from about 1:4 to about 1:2.

Oil dispersing nonionic surfactants suitable for inclusion in the compositions according to the present invention have excellent oil dispersing characteristics as demonstrated by microscopy and Immersion tests.

To demonstrate the suitability of a nonionic surfactant for incorporation in the compositions according to the present invention a test matrix including the test nonionic and all other composition ingredients is prepared. A portion of this prototype is then viewed under a microscope using a Nikon Optipot-2 Videomicrowatcher. Surfactants suitable for incorporation in the compositions according to the present invention typically produce homogeneous (opaque) product matrices in which the oil droplets have a diameter in the range of from about 1 microns to about 30 microns, preferably from about 2 microns to about 20 microns, more preferably from about 3 microns to about 10 microns.

In the Immersion Test the in-use characteristics of prototype matrices are assessed. In essence, 6 ml of prototype matrix is dispersed in 20 liters of water at 40° C. The physical appearance of the resulting solution is then assessed. Compositions which result in turbid (cloudy) solutions wherein no oil droplets are visible to the naked eye are regarded as demonstrating the desired behaviour, providing they additionally deliver the required skin feel.

Oil dispersing nonionic surfactants suitable for inclusion in the compositions according to the present invention are selected from C6–C19 polyhydroxy fatty acid amide surfactants, preferably C12–C16 polyhydroxy fatty acid amide surfactants, more preferably C12–C14 polyhydroxy fatty acid amide surfactants having the general formula (I).

The preferred polyhydroxy fatty acid amide surfactants are those in which $R_9$ is $C_{1-4}$ alkyl, preferably methyl, and $R_8$ is $C_7$–$C_{19}$ alkyl or alkenyl, more preferably straight-chain $C_9$–$C_{17}$ alkyl or alkenyl, or mixture thereof; and $Z_2$ is a polyhydroxyhydrocarbyl having a linear hydrocarbyl chain with at least 3 hydroxyls directly connected to the chain, or an alkoxylated derivative (preferably ethoxylated or propoxylated) thereof. $Z_2$ preferably will be derived from a reducing sugar in a reductive amination reaction; more preferably $Z_2$ is a glycityl. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for $Z_2$. It should be understood that it is by no means intended to exclude other suitable raw materials. $Z_2$ preferably will be selected from the group consisting of —$CH_2(CHOH)_n$—$CH_2OH$, —$CH(CH_2OH)$—$(CHOH)_{n-1}$—$CH_2OH$, —$CH_2$—$(CHOH)_2(CHOR')(CHOH)$—$CH_2OH$, where n is an integer from 3 to 5, inclusive, and R' is H or a cyclic or aliphatic monosaccharide, and alkoxylated derivatives thereof. Most preferred are glycityls wherein n is 4, particularly —$CH_2$—$(CHOH)_4$—$CH_2OH$.

In compounds of the above formula, $R_8$-CO—N< can be, for example, cocoamide, stearamide, oleamide, lauramide, myristamide, capricamide, palmitamide, tallowamide, etc.

A preferred process for making the above compounds having formula (I) comprises reacting a fatty acid triglyceride with an N-substituted polyhydroxy amine in the substantial absence of lower ($C_1$–$C_4$) alcoholic solvent, but preferably with an alkoxylated alcohol or alkoxylated alkyl phenol such as NEODOL and using an alkoxide catalyst at temperatures of from about 50° C. to about 140° C. to provide high yields (90–98%) of the desired products Suitable processes for making the desired polyhydroxy fatty acid amide materials are outlined in U.S. Pat. No. 5,194,639 and U.S. Pat. No. 5,380,891.

The most preferred polyhydroxy fatty acid amide has the formula $R_8(CO)N(CH_3)CH_2(CHOH)_4CH_2OH$ wherein $R_8$ is a C11–C17 straight chain alkyl or alkenyl group.

Applicant has found that bathing compositions containing the oil-dispersing nonionic surfactants as defined herein demonstrate excellent mildness, post-use skin feel and lathering characteristics. In addition such compositions also display good normal/high temperature stability under extended storage conditions. However, at low temperature (generally about 5° C. or less) the compositions demonstrate highly viscous gel-like characteristics reflecting the gel-forming behaviour of the oil-dispersing nonionic surfactant material.

Applicant has found that addition of conventional hydrotrope materials such as ammonium xylene sulphonate, sodium cumene sulphonate or propylene glycol to the compositions does not significantly limit the formation of low temperature gels.

A further essential feature of the compositions of the invention is an alkyl sulphate fluidising agent. Fluidising agents are of particular value in the compositions of the present invention for the provision of low temperature (generally about 5° C. or less) fluidity advantages. Applicant has found that compositions containing the fluidising agents and gel-forming surfactants according to the invention demonstrate improved fluidity under stressed low temperature conditions than compositions with no such agent.

Fluidising agents suitable for inclusion in the compositions of the present invention are selected from alkyl sulphate materials and mixtures thereof having the general formula (II);

R—OSO$_3$M wherein R is straight or branched chain alkyl, preferably straight chain containing on average from about 4 to about 10 carbon atoms, preferably from about 6 to about 10 carbon atoms and especially about 8 carbon atoms and wherein M is selected from alkali and alkali earth metals such as Na, K and Li and ammonium and alkanolamine salts and mixtures thereof. It should be understood that the definition of any particular carbon chain length, say C$_8$ is an average value and as such may contain certain proportions of both higher and lower carbon chain lengths as a direct function of the particular process conditions of its synthesis. Particularly preferred materials have a high proportion (>50% by weight) of the desired carbon chain length. More particularly about 80% or about 90%, and especially at least about 95% are preferred. The level of such material can be achieved by modification of the and the exact nature of the starting materials. Alkyl sulphate materials suitable for use in the present invention include C8 alkyl sulphate having at least about 99% by weight C8 material available from Albright and Wilson under the trade name Empimin LV33.

The compositions of the invention can optionally include a dispersed oil phase. The dispersed oil phase preferably comprises a mixture of oil components selected on the basis of their oil/surfactant solution interfacial tension characteristics, such combinations being optimum for delivering desirable emulsion stabilisation and skin deposition characteristics.

Oil/surfactant interfacial tension (IFT) measurements indicate the degree to which a surfactant solution can reduce the interfacial tension (IFT) between an oil component and a water phase. IFT measurements are made using a Spinning Drop Interfacial Tensiometer and are taken at 40–50° C. and 21 Degrees Clark water hardness (428 ppm CaCO$_3$) and 75 ppm aqueous surfactant solution concentration. In this test the surfactant system preferred for use is the surfactant system of the final cleansing composition. Where difficulties arise, or for screening purposes a standard aqueous surfactant solution can be used comprising a mixture of ethoxylated alkyl sulphate having two ethoxylated groups and alkyl N-methyl glucose amide in a weight ratio of about 4:1. Measurements are undertaken at pH 7 and are reported as the average of the 2, 5 and 10 minute interfacial tension readings.

By 'interfacial tension' (IFT) herein is meant the tension measured at the oil/water interface. IFT measurements using the spinning drop technique, are disclosed by Cafas, Schechter and Wade, "The Measurement of Low Interfacial Tension via the Spinning Drop Technique", ACS Symposium Series No.8 (1975) ADSORPTION AT INTERFACES, beginning at page 234.

The dispersed oil phase suitable for inclusion herein preferably comprises a mixture of oil components selected from polyol polyesters, hydrocarbons, lanolin and lanolin derivatives and animal and vegetable triglycerides. Use of a mixed oil system is valuable both for the effective emulsification of the oils within the product matrix and also for their subsequent deposition upon the skin surface upon product dilution in use. Applicant has found that compositions having mixed oil components as defined deliver improved skin feel both in use and after use versus products containing the individual oil components alone.

The total level of dispersed oil present is from about 1% to about 30%, preferably from about 3% to about 25%, more preferably from about 5% to about 20%, most preferably from about 8% to about 15% by weight. In compositions comprising a polyol polyester as a first oil component the weight ratio of polyol polyester oil component to further oil components is in the range of from about 20:1 to about 1:20, preferably from about 8:1 to about 1:8, more preferably from about 4:1 to about 1:4.

Suitable polyol polyester components are selected from nonocclusive liquid or liquifiable polyol fatty acid polyesters, especially nonocclusive liquid polyol fatty acid polyesters containing at least four fatty acid ester groups and wherein the polyol moiety is selected from sugars and sugar alcohols containing from about 4 to about 8 hydroxyl groups, and wherein each carboxylic acid moiety has from about 8 to about 22 carbon atoms and wherein the liquid polyol fatty acid polyester has a complete melting point of less than about 30° C.

The polyester also preferably has an oil/surfactant interfacial tension (IF) of greater than about 1.0 dynes/cm, preferably from about 1.1 to about 4.0, more preferably from about 1.2 to about 3.0 and especially from about 1.3 to about 2.0 dynes/cm (as measured under the above standard conditions) and is present at a level of from about 1% to about 10%, preferably from about 1% to about 5%, more preferably from about 2% to about 4% by weight.

The liquid polyol polyesters preferred for use in the present compositions comprise certain polyols, especially sugars or sugar alcohols, esterified with at least four fatty acid groups. Accordingly, preferred polyol starting material should have at least four esterifiable hydroxyl groups. Examples of preferred polyols are sugars, including monosaccharaides and disaccharides, and sugar alcohols. Examples of monosaccharides containing four hydroxyl groups are xylose and arabinose and the sugar alcohol derived from xylose, which has five hydroxyl groups, i.e., xylitol. The monosaccharide, erythrose, is not preferred in the practice of this invention since it only contains three hydroxyl groups, but the sugar alcohol derived from erythrose, i.e., erythritol, contains four hydroxyl groups and accordingly can be used. Suitable five hydroxyl group-containing monosaccharides are galactose, fructose, and sorbose. Sugar alcohols containing six —OH groups derived from the hydrolysis products of sucrose, as well as glucose and sorbose, e.g., sorbitol, are also suitable. Examples of disaccharide polyols which can be used include maltose, lactose, and sucrose, all of which contain eight hydroxyl groups.

Preferred polyols for preparing the polyesters for use in the present invention are selected from the group consisting of erythritol, xylitol, sorbitol, glucose, and sucrose. Sucrose is especially preferred.

The preferred polyol starting material having at least four hydroxyl groups is esterified on at least four of the —OH groups with a fatty acid containing from about 8 to about 22 carbon atoms. Examples of such fatty acids include caprylic, capric, lauric, myristic, myristoleic, palmitic, palmitoleic, stearic, oleic, ricinoleic, linoleic, linolenic, eleostearic, arachidic, arachidonic, behenic, and erucic acid. The fatty acids can be derived from naturally occurring or synthetic fatty acids; they can be saturated or unsaturated, including positional and geometrical isomers. However, in order to provide liquid polyesters preferred for use herein, at least about 50% by weight of the fatty acid incorporated into the polyester molecule should be unsaturated. Oleic and linoleic acids, and mixtures thereof, are especially preferred.

The polyol fatty acid polyesters useful in this invention preferably contain at least four fatty acid ester groups. It is not necessary that all of the hydroxyl groups of the polyol be esterified with fatty acid, but it is preferable that the polyester contain no more than two unesterified hydroxyl groups.

Most preferably, substantially all of the hydroxyl groups of the polyol are esterified with fatty acid, i.e., the polyol moiety is substantially completely esterified. The fatty acids esterified to the polyol molecule can be the same or mixed, but as noted above, a substantial amount of the unsaturated acid ester groups must be present to provide liquidity.

To illustrate the above points, a sucrose tetra-fatty acid ester would be suitable for use herein, but is not preferred because it has more than two unesterified hydroxyl groups. A sucrose hexa-fatty acid ester would be preferred because it has no more than two unesterified hydroxyl groups. Highly preferred compounds in which all the hydroxyl groups are esterified with fatty acids include the liquid sucrose octa-substituted fatty acid esters.

The following are non-limiting examples of specific polyol fatty acid polyesters containing at least four fatty acid ester groups preferred for use in the present invention: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof.

As noted above, highly preferred polyol fatty acid esters are those wherein the fatty acids contain from about 14 to about 18 carbon atoms.

The preferred liquid polyol polyesters preferred for use herein have complete melting points below about 30° C., preferably below about 27.5° C., more preferably below about 25° C. Complete melting points reported herein are measured by Differential Scanning Calorimetry (DSC).

The polyol fatty acid polyesters suitable for use herein can be prepared by a variety of methods well known to those skilled in the art. These methods include: transesterification of the polyol with methyl, ethyl or glycerol fatty acid esters using a variety of catalysts; acylation of the polyol with a fatty acid chloride; acylation of the polyol with a fatty acid anhydride; and acylation of the polyol with a fatty acid, per se. See U.S. Pat. No. 2,831,854; U.S. Pat. No. 4,005,196, to Jandacek, issued Jan. 25, 1977; U.S. Pat. No. 4,005,196, to Jandacek, issued Jan. 25, 1977.

The preferred polyol polyester oil component, where present, for the compositions according to the present invention is a liquid sucrose octa-substituted fatty acid ester.

The compositions of the present invention comprise further oil components as or in the dispersed oil phase. Highly preferred further oil components have an interfacial tension (IFT) in the range of from about 0.1 to about 1.0 dynes/cm, preferably from about 0.2 to about 0.9, more preferably from about 0.3 to about 0.7 dynes/cm (as measured using the above standard conditions) and are present at an individual level of from about 1% to about 20%, preferably from about 5% to about 15%, more preferably from about 8% to about 15% by weight.

Further oil components of the dispersed oil phase suitable for use herein include hydrocarbons, lanolin and animal and vegetable triglycerides such as mineral oils, petrolatum and squalene, fatty sorbitan esters (see U.S. Pat. No. 3,988,255, Seiden, issued Oct. 26th 1976), lanolin and oil-like lanolin derivatives, water-insoluble silicones inclusive of non-volatile polyalkyl and polyaryl siloxane gums and fluids, volatile cyclic and linear polyalkylsiloxanes, polyalkoxylated silicones, amino and quaternary ammonium modified silicones, rigid cross-linked and reinforced silicones and mixtures thereof, $C_1$–$C_{24}$ esters of $C_8$–$C_{30}$ fatty acids such as isopropyl myristate and cetyl ricinoleate, beeswax, saturated and unsaturated fatty alcohols such as behenyl alcohol, almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soyabean oil, avocado oil, safflower oil, coconut oil, hazelnut oil, olive oil, grapeseed oil, and sunflower seed oil, and $C_1$–$C_{24}$ esters of dimer and trimer acids such as diisopropyl dimerate, diisostearylmalate, diisostearyldimerate and triisostearyltrimerate and mixtures thereof.

The most preferred further oil components are non-polar oils selected from mineral oil, petrolatum, water-insoluble silicones, soya bean oil and the like and mixtures thereof. Especially preferred for use herein is mineral oil.

Anionic surfactants suitable for inclusion in the compositions of the invention can generally be described as mild synthetic detergent surfactants and include ethoxylated alkyl sulfates, alkyl glyceryl ether sulfonates, methyl acyl taurates, fatty acyl glycinates, N-acyl glutamates, acyl isethionates, alkyl sulfosuccinates, alkyl ethoxy sulphosuccinates, alpha-sulfonated fatty acids, their salts and/or their esters, alkyl ethoxy carboxylates, alkyl phosphate esters, ethoxylated alkyl phosphate esters, acyl sarcosinates and fatty acid/protein condensates, and mixtures thereof. Alkyl and/or acyl chain lengths for these surfactants are $C_{12}$–$C_{22}$, preferably $C_{12}$–$C_{18}$, more preferably $C_{12}$–$C_{14}$.

Preferred for use herein from the viewpoint of optimum mildness and lathering characteristics are the salts of sulfuric acid esters of the reaction product of 1 mole of a higher fatty alcohol and from about 1 to about 12 moles of ethylene oxide, with sodium, magnesium and ammonium being the preferred counterions. Particularly preferred are the alkyl sulfates containing from about 2 to 6, preferably 2 to 4 moles of ethylene oxide, such as sodium laureth-2 sulfate, sodium laureth-3 sulfate and magnesium sodium laureth-3.6 sulfate. In preferred embodiments, the anionic surfactant contains at least about 50%, especially at least about 75% by weight of ethoxylated alkyl sulfate.

The compositions for use herein suitably also contain an amphoteric surfactant. Amphoteric surfactants suitable for use in the compositions of the invention include:

(a) imidazolinium surfactants of formula (III)

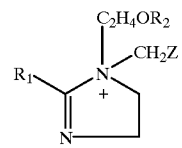

wherein $R_1$ is $C_7$–$C_{22}$ alkyl or alkenyl, $R_2$ is hydrogen or $CH_2Z$, each Z is independently $CO_2M$ or $CH_2CO_2M$, and M is H, alkali metal, alkaline earth metal, ammonium or alkanolammonium; and/or ammonium derivatives of formula (IV)

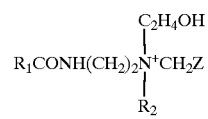

wherein $R_1$, $R_2$ and Z are as defined above;
(b) aminoalkanoates of formula (V)

$$R_1NH(CH_2)_nCO_2M$$

and iminodialkanoates of formula (VI)

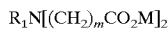

wherein n and m are numbers from 1 to 4, and $R_1$ and M are independently selected from the groups specified above; and (c) mixtures thereof.

Suitable amphoteric surfactants of type (a) are marketed under the trade name Miranol and Empigen and are understood to comprise a complex mixture of species. Traditionally, the Miranols have been described as having the general formula m, although the CTFA Cosmetic Ingredient Dictionary, 4th Edition indicates the non-cyclic structure IV. In practice, a complex mixture of cyclic and non-cyclic species is likely to exist and both definitions are given here for sake of completeness. Preferred for use herein, however, are the non-cyclic species.

Examples of suitable amphoteric surfactants of type (a) include compounds of formula III and/or IV in which $R_1$ is $C_8H_{17}$ (especially iso-capryl), $C_9H_{19}$ and $C_{11}H_{23}$ alkyl. Especially preferred are the compounds in which $R_1$ is $C_9H_{19}$, Z is $CO_2M$ and $R_2$ is H; the compounds in which $R_1$ is $C_{11}H_{23}$, Z is $CO_2M$ and $R_2$ is $CH_2CO_2M$; and the compounds in which $R_1$ is $C_{11}H_{23}$, Z is $CO_2M$ and $R_2$ is H.

In CTFA nomenclature, materials preferred for use in the present invention include cocoamphocarboxypropionate, cocoamphocarboxy propionic acid, and especially cocoamphoacetate and cocoamphodiacetate (otherwise referred to as cocoamphocarboxyglycinate). Specific commercial products include those sold under the trade names of Empigen CDL60 and CDR 60 (Albright & Wilson), Miranol H2M Conc. Miranol C2M Conc. N.P., Miranol C2M Conc. O.P., Miranol C2M SF, Miranol CM Special (Rhône-Poulenc); Alkateric 2CIB (Alkaril Chemicals); Amphoterge W-2 (Lonza, Inc.); Monateric CDX-38, Monateric CSH-32 (Mona Industries); Rewoteric AM-2C (Rewo Chemical Group); and Schercotic MS-2 (Scher Chemicals).

It will be understood that a number of commercially-available amphoteric surfactants of this type are manufactured and sold in the form of electroneutral complexes with, for example, hydroxide counterions or with anionic sulfate or sulfonate surfactants, especially those of the sulfated $C_8$–$C_{18}$ alcohol, $C_8$–$C_{18}$ ethoxylated alcohol or $C_8$–$C_{18}$ acyl glyceride types. Preferred from the viewpoint of mildness and product stability, however, are compositions which are essentially free of (non-ethoxylated) sulfated alcohol surfactants. Note also that the concentrations and weight ratios of the amphoteric surfactants are based herein on the uncomplexed forms of the surfactants, any anionic surfactant counterions being considered as part of the overall anionic surfactant component content.

Examples of suitable amphoteric surfactants of type (b) include salts, especially the triethanolammonium salts and salts of N-lauryl-beta-amino propionic acid and N-lauryl-imino-dipropionic acid. Such materials are sold under the trade name Deriphat by Henkel and Mirataine by Rhône-Poulenc. Amphoterics preferred for use herein, however, are those of formula m and/or IV.

The compositions of the invention may also include auxiliary nonionic surfactant. Suitable auxiliary nonionic surfactants for use herein can be selected from C12–C14 fatty acid mono-and diethanolamides and sucrose polyester surfactants, water soluble vegetable and animal-derived emollients (oil derived) such as triglycerides with a polyglycol chain inserted; ethoxylated mono and di-glycerides, polyethoxylated lanolins and shea butter derivatives and mixtures thereof. One preferred class of oil-derived auxiliary nonionic surfactants for use herein have the general formula (VI)

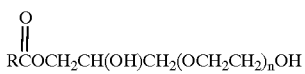

wherein n is from about 5 to about 200, preferably from about 20 to about 100, more preferably from about 30 to about 85, and wherein R comprises an aliphatic radical having on average from about 5 to 20 carbon atoms, preferably from about 9 to 18 carbon atoms.

Suitable ethoxylated oils and fats of this class include polyethyleneglycol derivatives of glyceryl cocoate, glyceryl caproate, glyceryl caprylate, glyceryl tallowate, glyceryl palmate, glyceryl stearate, glyceryl laurate, glyceryl oleate, glyceryl ricinoleate, and glyceryl fatty esters derived from triglycerides, such as palm oil, almond oil, and corn oil, preferably glyceryl tallowate and glyceryl cocoate.

Suitable oil derived auxiliary nonionic surfactants of this class are available from Croda Inc. (New York, U.S.A.) under their Crovol line of materials such as Crovol EP40 (PEG 20 evening primrose glyceride), Crovol EP 70 (PEG 60 evening primrose glyceride) Crovol A-40 (PEG 20 almond glyceride), Crovol A-70 (PEG 60 almond glyceride), Crovol M-40 (PEG 20 maize glyceride), Crovol M-70 (PEG 60 maize glyceride), Crovol PK-40 (PEG 12 palm kernel glyceride), and Crovol PK-70 (PEG 45 palm kernel glyceride) and under their Solan range of materials such as Solan E, E50 and X polyethoxylated lanolins. Further suitable surfactants of this class are commercially available from Sherex Chemical Co. (Dublin, Ohio, U.S.A.)/Witco (Rewo) under their Varonic LI and Rewoderm lines of surfactants. These include, for example, Varonic LI 48 (polyethylene glycol (n=80) glyceryl tallowate, alternatively referred to as PEG 80 glyceryl tallowate), Varonic LI 2 (PEG 28 glyceryl tallowate), Varonic LI 420 (PEG 200 glyceryl tallowate), and Varonic LI 63 and 67 (PEG 30 and PEG 80 glyceryl cocoates) and Rewoderm LI5-20 (PEG-200 palmitate), Rewoderm LIS 80 (PEG-200 palmitate with PEG-7 glyceryl cocoate), Rewoderm LIS 75 (PEG-200 tallowate with PEG-7 glyceryl cocoate) and mixtures thereof. Other water soluble vegetable-derived emollients suitable for use are PEG derivatives of corn, avocado and babassu oil as well as Softigen 767 (PEG-6 caprylic/capric glycerides).

Also suitable for use herein are auxiliary nonionic surfactants derived from composite vegetable fats extracted from the fruit of the Shea Tree (Butyrospermum Karkii Kotschy) and derivatives thereof. This vegetable fat, known as Shea Butter is widely used in Central Africa for a variety of means such as soap making and as a barrier cream, it is marketed by Sederma (78610 Le Perray En Yvelines, France). Also of interest are ethoxylated derivatives of Shea butter available from Karlshamn Chemical Co. (Columbos, Ohio, U.S.A.) under their Lipex range of chemicals, such as Lipex 102 E-75 (ethoxylated mono, di-glycerides of Shea butter) and from Croda Inc. (New York, U.S.A.) under their Crovol line of materials such as Crovol SB 70 (ethoxylated mono, di-glycerides of Shea butter). Similarly, ethoxylated derivatives of Mango, Cocoa and Illipe butter may be used in compositions according to the invention. Although these are classified as ethoxylated nonionic surfactants it is understood that a certain proportion may remain as non-ethoxylated vegetable oil or fat.

Other suitable oil-derived nonionic surfactants include ethoxylated derivatives of almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil.

Oil derived auxiliary nonionic surfactants highly preferred for use herein from the viewpoint of optimum mildness and skin feel characteristics are PEG 60 evening primrose triglycerides; PEG 55 lanolin polyethoxylated derivatives and ethoxylated derivatives of Shea butter.

The compositions herein preferably also contain a zwitterionic surfactant.

Betaine surfactants suitable for inclusion in the composition of the invention include alkyl betaines of the formula $R_5R_6R_7N^+(CH_2)_nM$ (VIII) and amido betaines of the formula (IX)

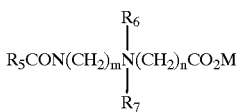

wherein $R_5$ is $C_{11}$–$C_{22}$ alkyl or alkenyl, $R_6$ and $R_7$ are independently $C_1$–$C_3$ alkyl, M is H, alkali metal, alkaline earth metal, ammonium or alkanolammonium, and n, m are each numbers from 1 to 4. Preferred betaines include cocoamidopropyldimethylcarboxymethyl betaine, laurylamidopropyldimethylcarboxymethyl betaine and Tego betaine (RTM).

Water-soluble auxiliary sultaine surfactants suitable for inclusion in the compositions of the present invention include alkyl sultaines of the formula (X);

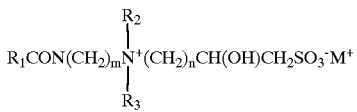

wherein $R_1$ is $C_7$ to $C_{22}$ alkyl or alkenyl, $R_2$ and $R_3$ are independently $C_1$ to $C_3$ alkyl, M is H, alkali metal, alkaline earth metal, ammonium or alkanolammonium and m and n are numbers from 1 to 4. Preferred for use herein is coco amido propylhydroxy sultaine.

Water-soluble auxiliary amine oxide surfactants suitable for inclusion in the compositions of the present invention include alkyl amine oxide $R_5R_6R_7NO$ and amido amine oxides of the formula (XI)

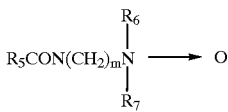

wherein $R_5$ is $C_{11}$ to $C_{22}$ alkyl or alkenyl, $R_6$ and $R_7$ are independently $C_1$ to $C_3$ alkyl, M is H, alkali metal, alkaline earth metal, ammonium or alkanolammonium and m is a number from 1 to 4. Preferred amine oxides include cocoamidopropylamine oxide, lauryl dimethyl amine oxide and myristyl dimethyl amine oxide.

The compositions of the invention may also contain a cationic or nonionic polymeric skin or hair conditioning agent at a level from about 0.01% to about 5%, preferably from about 0.04% to about 2% and especially from about 0.05% to about 1%. The polymer is found to be valuable for enhancing the creaminess and quality of the foam as well as providing a hair or skin conditioning utility.

Suitable polymers are high molecular weight materials (mass-average molecular weight determined, for instance, by light scattering, being generally from about 2,000 to about 3,000,000, preferably from about 5,000 to about 1,000,000).

Useful polymers are the cationic, nonionic, amphoteric, and anionic polymers useful in the cosmetic field. Preferred are cationic and nonionic polymers used in the cosmetic fields as hair or skin conditioning agents.

Representative classes of polymers include cationic and nonionic polysaccharides; cationic and nonionic homopolymers and copolymers derived from acrylic and/or methacrylic acid; cationic and nonionic hydroxyethyl cellulose resins; cationic copolymers of dimethyldiallylammonium chloride and acrylic acid; cationic homopolymers of dimethyldiallylammonium chloride; cationic polyalkylene and ethoxypolyalkylene imines; quaternized silicones, and mixtures thereof.

By way of exemplification, cationic polymers suitable for use herein include cationic guar gums such as hydroxypropyl trimethyl ammonium guar gum (d.s. of from 0.11 to 0.22) available commercially under the trade names Jaguar C-14S(RTM) and Jaguar C-17(RTM) and also Jaguar C-16 (RTM), which contains hydroxypropyl substituents (d.s. of from 0.8–1.1) in addition to the above-specified cationic groups, and quaternized cellulose ethers available commercially under the trade names Ucare Polymer JR and Celquat. Other suitable cationic polymers are homopolymers of dimethyldiallylammonium chloride available commercially under the trade name Merquat 100, copolymers of dimethyl aminoethylmethacrylate and acrylamide, copolymers of dimethyldiallylammonium chloride and acrylamide, available commercially under the trade names Merquat 550 and Merquat S, quaternized vinyl pyrrolidone acrylate or methacrylate copolymers of amino alcohol available commercially under the trade name Gafquat, and polyalkyleneimines such as polyethylenimine and ethoxylated polyethylenimine.

Nonionic polymers suitable for use in the compositions according to the present invention include any conventionally used nonionic polymer and preferably those of the Pluronic and Synperonic group of polyoxyethylene polyoxypropylene block copolymers available from BASF, such as Pluronic L-121 and ICI, such as synperonic PE-F127.

Anionic polymers suitable herein include hydrophobically-modified cross-linked polymers of acrylic acid having amphipathic properties as marketed by B F Goodrich under the trade name Pemulen TRI and Pemulen TR2; and the carboxyvinyl polymers sold by B F Goodrich under the trade mark Carbopol and which consist of polymers of acrylic acid cross-linked with polyallyl sucrose or polyallyl pentaeyrthritol, for example, Carbopol 934, 940 and 950.

Nonionic water-soluble cellulose ethers can be used as additional skin moisturising agents in the compositions according to the present inventions Widely used, commercially-available nonionic cellulose ethers include methyl cellulose, hydroxy propyl methyl cellulose, hydroxyethylcellulose, hydroxypropyl cellulose and ethyl hydroxyethyl cellulose. Particularly preferred for use as moisturisation aids are hydrophobically modified hydroxy ethyl cellulose materials. One commercially available material suitable for use herein is NATROSOL PLUS Grade 330 CS (RTM), a hydrophobically modified hydroxyethylcellulose available from Aqualon Company, Wilmington, Del. This material has a $C_{16}$ alkyl substitution of from 0.4% to 0.8% by weight. The hydroxyethyl molar substitution for this material is from 3.0 to 3.7. The average molecular weight for the water-soluble cellulose prior to modification is approximately 300,000. Another material of this type is sold under the trade name NATROSOL PLUS CS Grade D-67 (RTM), by Aqualon Company, Wilmington, Del. This material has a $C_{16}$ substitution of from 0.50% to 0.95%, by weight. The hydroxyethyl molar substitution for this material is from 2.3 to 3.7. The average molecular weight for the water soluble cellulose prior to modification is approximately 700,000.

The cleansing compositions can optionally include a hair or skin moisturizer which is soluble in the cleansing composition matrix. The preferred level of moisturizer is from about 0.5% to about 20% by weight. In preferred embodiments, the moisturizer is selected from:

1. water-soluble liquid polyols;
2. essential amino acid compounds found naturally occurring in the stratum corneum of the skin; and
3. water-soluble nonpolyol nonocclusives and mixtures thereof.

Some examples of more preferred nonocclusive moisturizers are glycerine, polyethylene glycol, propylene glycol, sorbitol, polyethylene glycol and propylene glycol ethers of methyl glucose (e.g. methyl glucam E-20), polyethylene glycol and propylene glycol ethers of lanolin alcohol (e.g. Solulan-75), sodium pyrrolidone carboxylic acid, lactic acid, urea, L-proline, guanidine, pyrrolidone, hydrolyzed protein and other collagen-derived proteins, aloe vera gel, acetamide MEA and lactamide MEA and mixtures thereof. Of the above, glycerine is highly preferred.

An additional optional component of the composition of the invention is an adduct prepared from vegetable oils containing non-conjugated polyunsaturated fatty acid esters which are conjugated and elaidinized and then modified via Diels-Alder addition with a member of the group consisting of acrylic acid, fumaric acid and maleic anhydride. The vegetable oil adduct preferably has the general formula (XII).

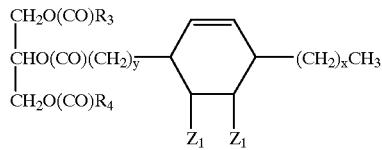

wherein x, y are integers of from 3 to 9, $R_3$ and $R_4$ are independently selected from saturated and unsaturated $C_7$–$C_{22}$ hydrocarbyl, each Z being $CO_2M$ and wherein M is H, or a salt forming cation, preferably alkalimetal, ammonium or alkanol ammonium. The adducts and their preparation are described in U.S. Pat. No. 4,740,367, the adducts being marketed under the trade name Ceraphyl GA (Van Dyke). The vegetable oil adduct is preferably added from about 0.01% to about 5%, preferably from about 0.05% to about 2%, more preferably from about 0.1% to about 1% by weight of the composition.

The compositions of the present invention can also include a fatty alcohol or fatty acid thickening agent having from about 12 to about 22 carbon atoms. Suitable fatty acid and fatty alcohol thickeners include Laurex NC (C12/14 fatty alcohol) available from Albright and Wilson and Priac 7908 (palm kernal fatty acid) available from Unichema.

The compositions according to the present invention can also include a stabilising system. Stabilising systems are valuable in the compositions of the invention for limitation of separation of oil components from the aqueous phase. Preferred stabilising systems suitable for inclusion in the compositions according to the present invention comprise a primary and secondary stabilising agent wherein the primary stabilising agent is an optionally modified clay or clay like material and the secondary stabilising agent is a hetero polysaccharide gum. Use of a mixed stabilising system is valuable for the delivery of lather having good volume, stability and appearance characteristics in combination with improvements in skin feel. The total level of primary and secondary stabilising agent present is from about 0.01% to about 15%, preferably from about 0.05% to about 12%, more preferably from about 0.1% to about 10% most preferably from about 0.5% to about 5% by weight wherein the ratio of primary stabiliser to secondary stabiliser is in the range of from about 32:1 to about 1:1, preferably from about 16:1 to about 1:1, more preferably from about 4:1 to about 2:1.

In preferred compositions according to the invention the primary stabiliser is a modified clay based material.

Suitable primary suspending agents for the compositions of the present invention include magnesium aluminium silicate ($Al_2Mg_8Si_2$), bentonite, hectorite and derivatives thereof. Magnesium aluminium silicate occurs naturally in such smectite materials as colerainite, saponite and sapphire. Refined magnesium aluminium silicate useful herein is available from the R. T. Vanderbilt Company, Inc. under the trade name Veegum (RTM) and from ECC America under the trade name Gelwhite MAS-H (RTM). Modified magnesium aluminium silicate materials such as magnesium aluminium silicate mineral/CMC are available from the R. T Vanderbilt Company, Inc. under the trade name Veegum Plus (RTM). This modified clay material contains smectite clay with sodium carboxymethylcellulose and titanium dioxide. Bentonite is a native hydrated colloidal aluminium silicate clay available from ECC America under the trade name Bentonite H (RTM) and from Whittaker, Clark and Daniels under the trade name Mineral Colloid BP 2430 (RTM). Hectorite is one of the montmorillonite minerals that is a principal constituent of bentonite clay. Hectorite is available from Rheox Inc. under the trade names Bentone EW (RTM) and Macaloid (RTM).

The preferred primary stabilising agent is magnesium aluminium silicate mineral/CMC available from the R.T. Vanderbilt Company, Inc. under the trade name Veegum Plus (RTM).

The preferred secondary stabilising agent in the compositions according to the invention is xanthan gum (xanthan/corn sugar gum) which is a heteropolysaccharide gum produced by a pure-culture fermentation of a carbohydrate with Xanthomonas campestris having a molecular weight of greater than about 1,000,000. It is believed to contain D-glucose, D-mannose and D-glucoronate in the molar ratios of 2.8:2.0:2.0. The polysaccharide is partially acetylated with 4.7% acetyl. This biosynthetic gum material is commercially available from Calgon under the trade name Kelgum CG (RTM) and from Kelko (a division of Merck & Co., Inc.), Meer and Vanderbilt under the respective trade names Keltrol (RTM), Merezan 8 (RTM) and Rhodigel (RTM) as well as from a variety of other sources. Xanthan gum mixtures are also available from Calgon, Alban Muller and others and are also suitable for inclusion in the compositions of the present invention. Further information on xanthan gum is to be found in Whistler, Roy L. (Editor) *Industrial Gums—Polysaccharides and Their Derivatives* New York: Academic Press, 1973.

A number of additional optional materials can be added to the cleansing compositions. Such materials include proteins and polypeptides and derivatives thereof; water-solubilizable preservatives such as DMDM Hydantoin, Germall 115, methyl, ethyl, propyl and butyl esters of hydroxybenzoic acid, EDTA, Euxyl (RTM) K400, Bronopol (2-bromo-2-nitropropane-1,3-diol), sodium benzoate and 2-phenoxyethanol; other moisturizing agents such as hyaluronic acid, chitin, and starch-grafted sodium polyacrylates such as Sanwet (RTM) IM-1000, IM-1500 and IM-2500 available from Celanese Superabsorbent Materials, Portsmith, Va., U.S.A. and described in U.S. Pat. No. 4,076,663; solvents such as hexylene glycol and propylene glycol; anti-bacterial agents such as Oxeco (phenoxy isopropanol); low temperature phase modifiers such as ammonium ion sources (e.g. $NH_4Cl$); viscosity control agents such as magnesium sulfate and other electrolytes; colouring agents; pearlescers and opacifiers such as ethylene glycol distearate, $TiO_2$ and $TiO_2$-coated mica; perfumes and perfume solubilizers such as procetyl AWS (PPG-5 ceteth-20), Cremaphor RH60 (PEG-60 hydrogentated castor oil); and zeolites such as Valfour BV400 and derivatives thereof and $Ca^{2+}/Mg^{2+}$ sequestrants such as polycarboxylates, amino polycarboxylates, polyphosphates, polyhosphonates, amino polyphosphonates and gluconates etc and pH adjusting agents such as citric acid and salts thereof. Water is also present at a level preferably of from about 20% to about 98.9% preferably at least about 50% by weight of the compositions herein.

The pH of the compositions is preferably from about 4 to about 8.

The invention is illustrated by the following non-limiting examples. In the examples, all concentrations are on a 100% active basis an the abbreviations have the following designation:

| | |
|---|---|
| Oil 1 | Liquid sucrose octaoleate having a complete melting point of less than about 30° C. and an IFT of about 1.45 dynes/cm (on a 4:1 anionic : GA aqueous solution basis) wherein IFT is measured as described herein. |
| Oil 2 | Mineral Oil having an IFT of about 0.38 (measured as detailed for Oil 1). |
| GA | Polyhydroxy fatty acid amide of formula I in which $R_8$ is $C_{11}$–$C_{17}$ alkyl, $R_9$ is methyl, and $Z_2$ is $CH_2(CHOH)_4CH_2OH$ |
| Anionic | Sodium laureth-2 sulfate |
| Amphoteric | Empigen CDL 60 - an aqueous mixture of 23.5% cocoamphoacetate (in which $R_1$ is coconut alkyl, $R_2$ is H, and Z is $CO_2Na$) and 1.35% cocoamphodiacetate (in which $R_1$ is coconut alkyl, $R_2$ is $CH_2CO_2Na$ and Z is $CO_2Na$). |
| Betaine | Cocoamidopropyldimethylcarboxymethylbetaine |
| Solan | Solan RTM) E (PEG 55 lanolin) |
| Ceraphyl GA | vegetable oil adduct obtained from non-conjugated poly unsaturated fatty acid esters which are conjugated then elaidinized. |
| Preservative | sodium benzoate |
| Stabiliser | MgAl silicate/CMC (Veegum Plus)/Xanthan Gum |
| Fluidising agent | Sodium $C_8$ Alkyl Sulphate |

EXAMPLES I TO VII

The following are personal cleansing compositions in the form of shower gel or bath foam products and which are representative of the present invention:

| | I | II | III | IV | V | VI | VII |
|---|---|---|---|---|---|---|---|
| GA | 8.0 | 5.0 | 4.0 | 4.0 | 5.0 | 6.0 | 4.0 |
| Anionic | 3.0 | 2.0 | 3.0 | 2.0 | 3.0 | 0.5 | 5.0 |
| Amphoteric | — | — | 1.0 | — | — | 0.5 | — |
| Betaine | 2.0 | 2.0 | — | 3.0 | 1.5 | 1.0 | — |
| Oil 1 | — | — | — | 5.0 | — | 8.0 | 5.0 |
| Oil 2 | 10.0 | — | 20.0 | 10.0 | — | 12.0 | — |
| Solan | — | — | — | — | 1.0 | — | — |
| Ceraphyl | — | — | — | 0.5 | 1.0 | 2.0 | — |
| Fluidiser | 2.0 | 2.0 | 1.0 | 1.5 | 0.5 | 1.5 | 1.5 |
| Stabiliser | — | — | — | 0.5 | 1.0 | 2.0 | — |
| Na Citrate | 1.0 | — | — | — | 2.0 | 1.5 | — |
| Perfume | 1.5 | 1.5 | 1.5 | 1.5 | 1.5 | 1.5 | 1.5 |
| Preservative | 0.25 | 0.25 | 0.25 | 0.25 | 0.25 | 0.25 | 0.25 |
| Water | | | | to 100 | | | |

Compositions I to VII are prepared by first hydrating any Veegum type material as a pre-mix. Next all of the oil materials are separately blended together using by stirring with water at ambient temperature. If xanthan gum type material is present it may be slurried by stirring with this mixture. Separately, the surfactant materials are hydrated along with any additional skin feel agents, preservatives and hydrotropes by mixing with water and heating to between about 20° C. and about 90° C. Finally, the oil blend is added to the hydrated Veegum pre-mix (if present) and then the stirred surfactant mixture is added to the combined mixture and this final blend is stirred and cooled to ambient temperature and the remaining water, preservatives, perfume and any other materials are added.

Finally, the compositions have a viscosity (Helipath, Spindle A, 10 rpm, 25° C., neat) in the range from 500 to 10,000 cps, preferably from about 1,000 to about 4,000 cps.

The products provide excellent in-use and efficacy benefits including excellent low temperature fluidity characteristics, good skin feel during and after use, good lather volume and stability characteristics, skin conditioning, mildness, cleansing, good water-feel and appearance.

We claim:
1. A personal cleansing composition comprising:
   (a) from about 1% to about 25% by weight of an oil-dispersing, water-soluble gel-forming nonionic surfactant;
   (b) from about 0.1% to about 3% by weight of alkyl sulphate fluidising agent having the general formula: R—$OSO_3M$, wherein R is a straight or branched chain alkyl having an average of from 4 to 8 carbon atoms; and
   (c) from about 1% to about 30% by weight of a dispersed oil phase.
2. A personal cleansing composition according to claim 1 comprising:
   (a) from about 1.5% to about 10% by weight of the gel forming nonionic surfactant;
   (b) from about 0.1% to about 15% by weight of water-soluble auxiliary surfactant selected from the group consisting of other nonionic, anionic, zwitterionic and amphoteric surfactants having on
   (c) from about 0.1% to about 3% by weight of fluidising agent;
   (d) from about 4.5% to about 30% by weight of dispersed oil phase; and
   (e) water,
wherein the ratio of auxiliary surfactant to gel-forming nonionic surfactant is in the range of from about 1:100 to about 2:1 by weight and the ratio of gel-forming nonionic surfactant to dispersed oil is from about 1:20 to about 3:2 by weight.

3. A composition according to claim 1 wherein the composition has a viscosity (Helipath, Spindle A, 10 rpm, 25° C., neat) in the range from 500 to 10,000 cps.

4. A composition according to claim 1 wherein the gel-forming nonionic surfactant is selected from the group consisting of C6–C19 polyhydroxy fatty acid amide surfactants having the general formula (I);

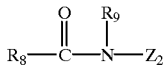

wherein $R_9$ is $C_{1-4}$ alkyl, and $R_8$ is $C_7$–$C_{19}$ alkyl or alkenyl, or mixture thereof; and $Z_2$ is a polyhydroxyhydrocarbyl having a linear hydrocarbyl chain with at least 3 hydroxyls directly connected to the chain, or an alkoxylated derivative thereof.

5. A composition according to claim 1 wherein the gel-forming nonionic surfactant is a C12–C14 polyhydroxy fatty acid amide.

6. A composition according to claim 1 wherein the gel-forming nonionic surfactant is a polyhydroxy fatty acid amide having the formula $R_8(CO)N(CH_3)CH_2(CHOH)_4CH_2OH$ wherein $R_8$ is a C12–C17 straight chain alkyl or alkenyl group.

7. A composition according to claim 1 comprising from about 2% to about 9% by weight of the gel-forming nonionic surfactant.

8. A composition according to claim 1 wherein the fluidising agent is $C_8$ alkyl sulphate.

9. A composition according to claim 1 wherein the dispersed oil phase comprises a first oil component having an oil/surfactant solution interfacial tension (IFT) of greater than about 1.0 dynes/cm and a second oil component having an oil/surfactant solution interfacial tension (IFT) in the range of from about 0.1 to about 1.0 dynes/cm.

10. A composition according to any of claim 9 wherein the first oil component is selected from the group consisting of glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof.

11. A composition according to claim 10 wherein the first oil component is sucrose octaoleate.

12. A composition according to any of claim 9 wherein the first oil component is present at a level of from about 1% to about 10% by weight.

13. A composition according to claim 1 wherein the dispersed oil phase has an oil/surfactant interfacial tension (IFT in the range of from about 0.1 to about 1.0 dynes/cm.

14. A composition according to any of claim 13 wherein the dispersed phase comprises one or more oils selected from the group consisting of hydrocarbons, animal and vegetable triglycerides, lanolin and lanolin derivatives, water-insoluble silicones inclusive of non-volatile polyalkyl and polyaryl siloxane gums and fluids, volatile cyclic and linear polyalkylsiloxanes, polyalkoxylated silicones, amino and quaternary ammonium modified silicones, rigid cross-linked and reinforced silicones and mixtures thereof, $C_1$–$C_{24}$ esters of $C_8$–$C_{30}$ fatty acids, beeswax, saturated and unsaturated fatty alcohols, almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil, and $C_1$–$C_{24}$ esters of dimer and trimer acids and mixtures thereof.

15. A composition according to claim 1 wherein the disperse phase comprises one or more oils selected from the group consisting of mineral oil, petrolatum, water insoluble silicones, soya bean oil and mixtures thereof.

16. A composition according to claim 9 wherein the oil components are present at an individual level of from about 1% to about 20% by weight.

17. A composition according to claim 1 wherein the total level of oil in the dispersed oil phase is from about 3% to about 25% by weight.

18. A composition according to claim 1 wherein the ratio of gel-forming nonionic surfactant to dispersed oil phase is in the range from about 1:8 to about 1:1 by weight.

19. A composition according to claim 1 comprising a mixture of gel-forming nonionic, anionic and optionally other nonionic, zwitterionic and amphoteric surfactants together with mineral oil.

20. A composition according to any of claim 1 comprising from about 0.5% to about 8% by weight in total of auxiliary surfactant.

21. A composition according to claim 1 wherein the anionic surfactant is selected from the group consisting of ethoxylated alkyl sulfates, alkyl glyceryl ether sulfonates, methyl acyl taurates, fatty acyl glycinates, alkyl ethoxy carboxylates, N-acyl glutamates, acyl isethionates, alkyl sulfosuccinates, alkyl ethoxy sulphosuccinates, alpha-sulfonated fatty acids, their salts and/or their esters, alkyl phosphate esters, ethoxylated alkyl phosphate esters, acyl sarcosinates and fatty acid/protein condensates, and mixtures thereof.

22. A composition according to claim 2 wherein the anionic surfactant comprises an ethoxylated $C_{12}$–$C_{22}$ alkyl sulfate.

23. A composition according to claim 2 wherein the amphoteric surfactant is selected from:
(a) imidazolinium derivatives of formula (III)

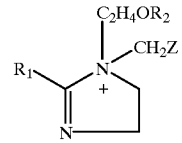

wherein $R_1$ is $C_7$–$C_{22}$ alkyl or alkenyl, $R_2$ is hydrogen or $CH_2Z$, each Z is independently $CO_2M$ or $CH_2CO_2M$, and M is H, alkali metal, alkaline earth metal, ammonium or alkanolammonium; and/or ammonium derivatives of formula (IV)

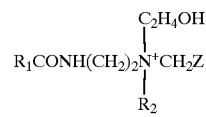

wherein $R_1$, $R_2$ and Z are as defined above:
(b) aminoalkanoates of formula (V)

and iminodialkanoates of formula (VI)

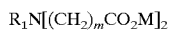

wherein n and m are numbers from 1 to 4, and $R_1$ and M are independently selected from the groups specified in (a) above; and (c) mixtures thereof.

24. A composition according to claim 23 wherein the amphoteric is selected from the imidazolinium derivatives of formula III and/or ammonium derivatives of formula IV.

25. A composition according to claim 2 wherein the zwitterionic surfactant is selected from alkyl betaine, amido betaine, alkyl sultaine and mixtures thereof.

26. A composition according to claim 2 wherein the weight ratio of anionic surfactant:other nonionic, zwitterionic and/or amphoteric surfactant is in the range from about 1:2 to about 6:1.

27. A composition according to claim 2 wherein the total combined level of gel-forming nonionic surfactant and auxiliary surfactant is from about 7% to about 20% by weight.

* * * * *